United States Patent [19]
Mason

[11] Patent Number: 5,348,032
[45] Date of Patent: Sep. 20, 1994

[54] ANTI-WICKING FLOSSING TOOL

[76] Inventor: Robert F. Mason, 10763 Hedda Pl., Cerritos, Calif. 90701

[21] Appl. No.: 100,282

[22] Filed: Aug. 2, 1993

[51] Int. Cl.⁵ ............................................. A61C 15/00
[52] U.S. Cl. ...................... 132/325; 132/323; 132/324
[58] Field of Search ............... 132/323, 324, 325, 326, 132/327

[56] References Cited

U.S. PATENT DOCUMENTS

| | | | |
|---|---|---|---|
| 1,274,423 | 8/1918 | Kristmann | 132/324 |
| 1,468,942 | 9/1923 | Gamble | 132/324 |
| 1,608,212 | 11/1926 | Hochstadter | 132/326 |
| 1,700,550 | 1/1929 | Stafford | 132/325 |
| 1,966,463 | 7/1934 | Rose | 132/324 |
| 1,990,404 | 2/1935 | Doner | 132/326 |
| 3,734,107 | 5/1973 | Thierman | 132/325 |
| 3,746,017 | 7/1973 | Casselman | 132/325 |
| 3,830,247 | 8/1974 | Kaphalakos | 132/325 |
| 3,886,956 | 6/1975 | Cash | 132/325 |
| 4,657,034 | 4/1987 | Koski | 132/324 |
| 5,044,386 | 9/1991 | Nelson | 132/324 X |

*Primary Examiner*—Gene Mancene
*Assistant Examiner*—Nicholas D. Lucchesi
*Attorney, Agent, or Firm*—Robert M. Sperry

[57] ABSTRACT

An improved dental flossing tool having a resilient member, located adjacent the tip where the flossing material exits the tool, and formed with an aperture of lesser diameter than that of the floss which serves to clamp the flossing material to positively prevent the floss from serving as a wick to carry moisture through the tip into the interior of the flossing tool.

20 Claims, 1 Drawing Sheet

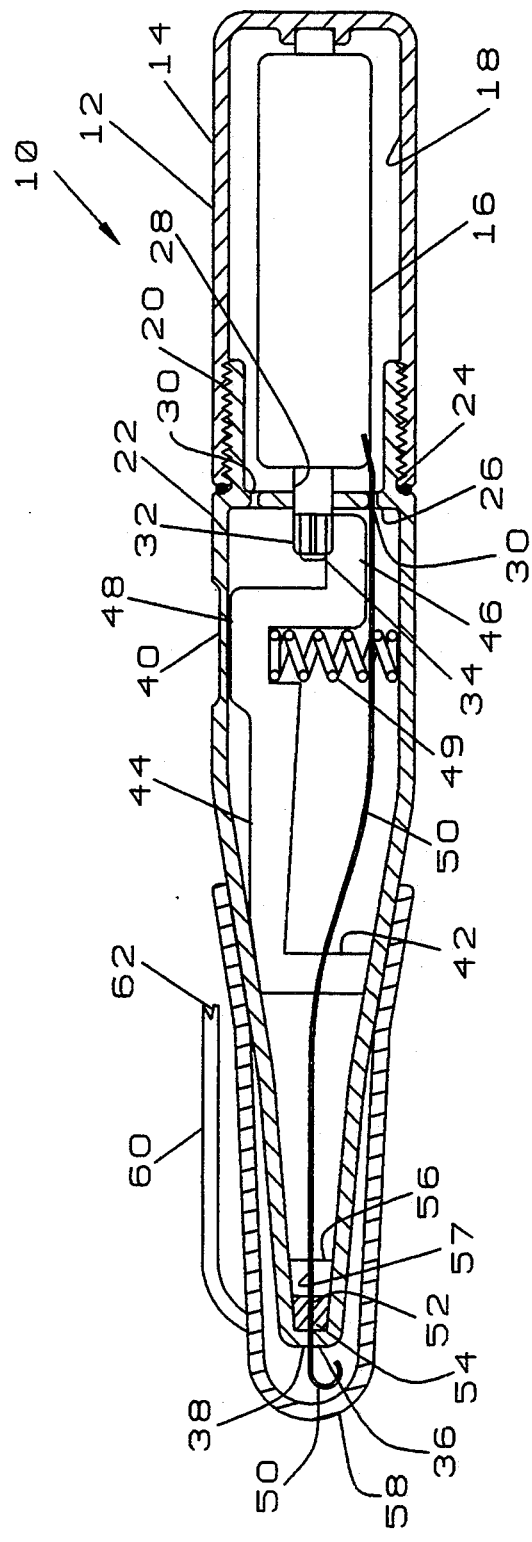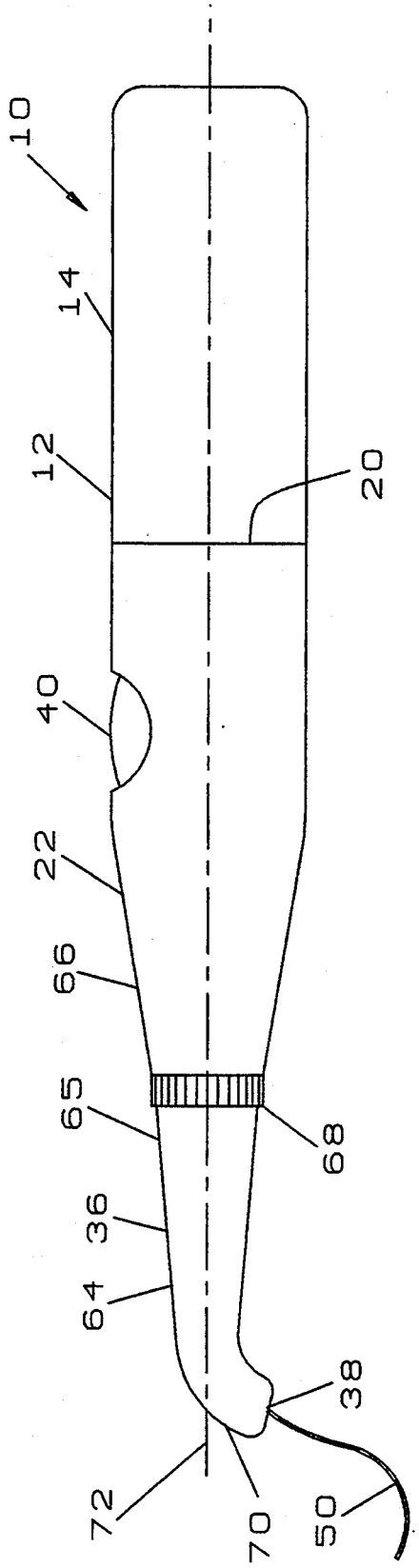

ANTI-WICKING FLOSSING TOOL

BACKGROUND

1. Field of Invention

This invention relates to dental flossing tools and is particularly directed to improved dental flossing tools having means for preventing the floss from serving as a wick to carry external moisture into the tool.

2. Prior Art

As is well known, the flossing of teeth is a very important part of proper dental hygiene. Unfortunately, many people fail to follow this procedure or perform the flossing operation incorrectly or inefficiently. Numerous types of dental flossing tools have been proposed heretofore to overcome these problems. One major problem that has been encountered in the use of dental floss is the fact that, despite the fact that dental floss is usually used in proximity to water, it is undesirable for the flossing material to become wet. Unfortunately, dental flossing material is highly absorptive and attracts moisture like a wick. However, air-borne moisture frequently carries germs, bacteria, etc. and, especially if the flossing material is stored in a dark area having poor air circulation, such as the interior of many prior art flossing tools, this provides an ideal environment for growth and development of such contaminants. Obviously, this situation is undesirable and may even be dangerous to the user. Thus, none of the prior art dental flossing tools has been entirely satisfactory.

BRIEF SUMMARY AND OBJECTS OF THE INVENTION

These disadvantages of prior art dental flossing tools are overcome with the present invention and an improved dental flossing tool is provided which positively precludes moisture from entering the tool to reach the floss material storage area. In fact, it has been found that the dental flossing tool of the present invention can be safely used, even while the user is taking a shower, without permitting moisture to enter the dental floss material storage area.

The advantages of the present invention are preferably attained by providing an improved dental flossing tool having resilient means, located adjacent the tip where the flossing material exits the tool, and formed with an aperture of lesser diameter than that of the floss which serves to clamp the flossing material to positively prevent the floss from serving as a wick to carry moisture through the tip into the interior of the flossing tool.

Accordingly, it is an object of the present invention to provide an improved dental flossing tool.

Another object of the present invention is to provide an improved dental flossing tool having an internal storage area for flossing material and having means for preventing moisture from entering the interior of the tool to reach the flossing material within the storage area.

A further object of the present invention is to provide an improved dental flossing tool having a tip where flossing material exits the tool and having means located adjacent the tip for preventing moisture from passing through the tip to the interior of the tool.

An additional object of the present invention is to provide an improved dental flossing tool having a tip where flossing material exits the tool and having means located adjacent the tip for preventing the floss from serving as a wick to carry moisture into the interior of the flossing tool.

A specific object of the present invention is to provide an improved dental flossing tool having resilient means, located adjacent the tip where the flossing material exits the tool, and formed with an aperture having a diameter no greater than that of the floss which serves to clamp the flossing material to positively prevent the floss from serving as a wick to carry moisture through the tip into the interior of the flossing tool. The resilient means may extend outside the tip to also serve as a cushion so as to prevent injury to the gums by striking the tool against the gums.

These and other objects and features of the present invention will be apparent from the following detailed description, taken with reference to the figures of the accompanying drawing.

BRIEF DESCRIPTION OF THE DRAWING

FIG. 1 is a longitudinal section through a dental flossing tool embodying the present invention; and FIG. 2 is a side view of an alternative form of the dental flossing tool of FIG. 1.

DETAILED DESCRIPTION OF THE INVENTION

In that form of the present invention chosen for purposes of illustration in FIG. 1, a dental flossing tool, indicated generally at 10, is shown comprising a generally cylindrical, hollow handle 12 having a removable rear end portion 14 to permit a spool 16 of dental flossing material to be loaded into or removed from a storage area 18 within the rear end portion 14 of the handle 12. As seen at 20, the rear end 14 is threadedly joined to the front portion 22 of the handle 12 and, if desired, suitable means, such as O-ring 24 may be provided to seal the joint 20 to prevent moisture from entering the storage area 18 through the joint 20. The front portion 22 of the handle 12 has a spider-like structure 26 formed with a central opening 28 and one or more peripheral openings 30. The floss spool 16 has a neck 32, which projects through the central opening 28 of the spider 26 and is freely rotatable therein. Also, the neck 32 is formed with a plurality of longitudinal ridges 34. The front portion 22 of the handle 12 tapers forwardly from the joint 20 to form a tip 36 having an opening 38 formed therein and is formed with an area 40 on one side of the front portion 22 of the handle 12, which is formed sufficiently thin to be somewhat flexible. Within the front portion 22, is a collar 42 having a self-sprung lever 44 formed integral with the collar 42 and projecting rearwardly from the collar 42. The lever 44 is somewhat resilient and is formed with an inwardly ribbed arcuate projection 46, which is engageable with the ridges 34 of the neck 32 of the floss spool 16 to prevent rotation of the spool 16. Also, the self-sprung lever 44 is formed with a button portion 48 which lies immediately adjacent the area 40 within the handle 12, so that depression of the area 40 will cause radially inward movement of the button portion 48 and, hence, of the self-sprung lever 44 and will cause the projection 46 to disengage from the ridges 34 of the neck 32 of the floss spool 16 to allow the floss spool 16 to rotate. This will completely seal the release button 48 from outside moisture. If desired, additional resilient means, such as spring 49, may be provided to assist in actuating the self-sprung lever 44. A strand 50 of the flossing material from the spool 16 is threaded through one of the openings 30 of the spider 26 and travels forwardly through the interior of front portion 22 of the handle 12. The floss strand 50 passes through resilient member 52, which is mounted at the tip 36 and is formed with an opening 54 extending axially through the member 52, and exits through opening 38 in the tip 36 of the front portion 22. The opening 54 of the resilient member 52 is of lesser diameter than that of the floss 50. Consequently, the resilient member 52 clamps tightly about the floss strand 50. In addition, if desired, a second member 56 may be mounted within the tip 36 adjacent the resilient member 52, formed of absorbent material and having an axial opening 57 of equal or lesser diameter than the floss strand 50. As seen in FIG. 1, the floss strand 50 passes through the second member 56 before passing through the resilient member 52 and exiting the tip 36 through opening 38. Finally, if desired, a tubular cap 58 may be provided which is frictionally engageable with the exterior of the front portion 22 of the handle 12. The cap 58 serves to protect the tip 36 and the portion of the floss strand 50 which projects from the opening 38 from contamination, yet can be removed quickly and easily to allow use of the flossing tool 10. A pocket clip 60, similar to that of a conventional writing pen, may be provided on the cap 58 and the end 62 of the clip 60 may be formed to provide a cutting device for the floss 50.

In use, the rear portion 14 of the handle 12 is removed and a spool 16 of dental floss is inserted into the storage area 18 of the rear portion 14. The neck 32 of the floss spool 16 is then inserted through the central opening 28 of the spider 26 of the front portion 22 of the handle 12 and the ridges 34 of the neck 32 engage the inwardly ribbed arcuate projection 46 of the lever 44, which prevents unwanted rotation of the floss spool 16. The floss strand 50 is passed through one of the peripheral openings 30 of the spider 26 and is passed forwardly through the interior of the front portion 22 of handle 12 to pass through opening 57 of the absorbent second member 56 and through opening 54 of the resilient member 52, before exiting the tip 36 through opening 38. To draw an additional quantity of the floss strand 50 from the spool 16, the user depresses the thin area 40 on the side of the front portion 22 of the handle 12. This forces the button portion 48 of the lever 44 radially inward, which serves to move the inwardly ribbed projection 46 out of engagement with the ridges 34 of neck 32 of the floss spool 16, which allows rotation of the floss spool 16 to facilitate withdrawal of the floss strand 50 from the spool 16. Because the opening 54 of the resilient member 52 is of lesser diameter than that of the floss strand 50, the resilient member 52 constantly squeezes tightly against the floss strand 50. This prevents any wicking action by the floss strand 50 and, hence, prevents external moisture from being carried into the interior of the tool 10 by the flossing strand 50. If any moisture should manage to get past the resilient member 52, the absorbent second member 56 serves to absorb such moisture, as additional insurance against the passage of moisture into the storage area 18 of the tool 10. When the user has finished performing the flossing operation, they can use the cutter 62 on the end of the clip 60 to sever the floss strand 50 and can frictionally engage the cap 60 over tip 36 of the tool 10 to prevent contamination until the tool 10 is needed for a subsequent flossing operation.

If desired, the floss strand 50 may be drawn through opening 38 of the tip 36 and, thereafter, the resilient member 52 may be formed by dipping, spraying, injecting or otherwise applying the resilient material to the tip 36 in liquid form, such as latex, and allowing the liquid material to solidify and set in situ surrounding the floss strand 50. As a result, the resilient member will firmly grip the floss strand 50. After the material of the resilient member 52 has solidified, pulling the floss strand 50 out of tip 36 for use will free the floss strand 50 from the solidified material of the resilient member 52, thereby forming the opening 54 of the resilient member 52 with a lateral dimension equal to or smaller than that of the floss strand 50. Thereafter, the resilient member 52 will grip the floss strand 50 and will function, in the manner described above, to prevent moisture from entering the tool 10 through opening 38 of the tip 36 or by the wicking action of the floss strand 50.

FIG. 2 shows an alternative form of the dental flossing tool of FIG. 1. In this form of the invention, the tip 36 is formed separate from the front portion 22, as seen at 65 in FIG. 2, and is rotatably connected to the main portion 66, adjacent the collar 42, by suitable means such as lock nut 68. As is well known, rotation of the lock nut 68, in a first direction, will release the tip 64 for rotation with respect to the main portion 66; while rotation of the lock nut 68, in the opposite direction will firmly clamp the tip 64 to the main portion 66 to prevent undesired rotation of the tip 64 with respect to the main portion 66. As seen in FIG. 2, the front end 70 of the tip 64 is bent to one side, so that the floss strand 50 exits opening 38 at an angle to the longitudinal axis 72 of the tool 10, rather than parallel with the axis 72, as in FIG. 1.

Obviously, numerous other variations and modifications can be made without departing from the spirit of the present invention. Therefore, it should be clearly understood that the forms of the present invention described above and shown in the figures of the accompanying drawing are illustrative only and are not intended to limit the scope of the present invention.

What is claimed is:

1. A dental flossing tool comprising:
a hollow handle containing a floss storage area therein and formed with a rigid tip having an opening and having a strand of floss entending from said storage area and exiting through said opening of said tip, and
a resilient member mounted adjacent said opening at the extreme end of said tip where said floss makes it's final exit from said tool and having an opening having a fixed lateral dimension no greater than that of said floss strand extending through said resilient member to cause said resilient member to clamp said strand of floss extending through said resilient member and to prevent moisture from entering said tool.

2. The flossing tool of claim 1 further comprising:
a spool of dental floss contained in said storage area with said strand of said dental floss extending from said spool through the interior of said tool and said opening of said resilient member and exiting through the opening of said tip.

3. The flossing tool of claim 2 further comprising:
means within said handle for preventing undesired movement of said floss strand.

4. The flossing tool of claim 3 wherein:
said means serves to prevent rotation of said spool.

5. The flossing tool of claim 4 wherein:
said spool has a ridged neck, and said means has an arcuate projection formed with a plurality of ribs engageable with the ridged neck and normally urged into engagement with said neck to prevent movement of said spool, and actuator means operable to move said projection out of engagement with said neck to allow rotation of said spool.

6. The flossing tool of claim 5 wherein:

said actuator means is integral with said arcuate projection and has a button portion moveable by the user to cause movement of said projection.

7. The flossing tool of claim 6 wherein:

said actuator means is located within said handle, and said handle has an area adjacent said actuator means formed sufficiently flexible to seal and allow movement of said button portion by pressing said area of said handle.

8. The flossing tool of claim 1 further comprising:

said tip is separate from said handle and is rotatably mounted externally on said handle.

9. The flossing tool of claim 8 further comprising:

a lock ring operable to lock said tip in a desired position of rotation with respect to said handle.

10. The flossing tool of claim 1 wherein:

said tip extends at an angle to the longitudinal axis of said handle.

11. The flossing tool of claim 1 further comprising:

a quantity of absorbent material mounted within said tip.

12. The flossing tool of claim 11 wherein:

said absorbent material is mounted adjacent said resilient member.

13. The flossing tool of claim 11 wherein:

said floss strand passes through said absorbent material between said storage area and said opening of said tip.

14. The flossing tool of claim 1 further comprising:

a cap frictionally engageable with said handle to cover said tip and having a clip for retaining said tool in a user's pocket.

15. The flossing tool of claim 14 wherein:

said clip has an end formed for cutting said floss strand.

16. The flossing tool of claim 1 wherein:

said resilient member clamps said floss strand sufficiently tightly to prevent wicking of moisture by said strand into the interior of said tool.

17. The flossing tool of claim 1 wherein:

the portion of said handle containing said storage area is removably connected to the other portions of said tool.

18. The flossing tool of claim 1 wherein:

said opening in said resilient member has a lateral dimension less than that of said floss strand.

19. The flossing tool of claim 18 wherein:

said resilient member is formed by drawing said floss strand through said tip opening, applying a quantity of liquid resilient material at said tip, and allowing said liquid resilient material to solidify and set in situ.

20. The flossing tool of claim 1 wherein:

said resilient member is formed by drawing said floss strand through said tip opening, applying a quantity of liquid resilient material at said tip, and allowing said liquid resilient material to solidify and set in situ.

* * * * *